(12) United States Patent
Frances

(10) Patent No.: US 7,129,282 B2
(45) Date of Patent: *Oct. 31, 2006

(54) DENTAL COMPOSITION BASED ON A FUNCTIONALIZED SILICONE CROSSLINKABLE AND/OR POLYMERIZABLE BY HEAT-PROCESS

(75) Inventor: Jean-Marc Frances, Meyzieu (FR)

(73) Assignee: Rhodia-Chimie, Aubervilliers (FR)

( * ) Notice: Subject to any disclaimer, the term of this patent is extended or adjusted under 35 U.S.C. 154(b) by 349 days.

This patent is subject to a terminal disclaimer.

(21) Appl. No.: 10/450,492

(22) PCT Filed: Dec. 18, 2001

(86) PCT No.: PCT/FR01/04044

§ 371 (c)(1), (2), (4) Date: Oct. 17, 2003

(87) PCT Pub. No.: WO02/051357

PCT Pub. Date: Jul. 4, 2002

(65) Prior Publication Data

US 2004/0048975 A1    Mar. 11, 2004

(30) Foreign Application Priority Data

Dec. 22, 2000   (FR)   ................... 00 16922

(51) Int. Cl.
C08G 77/08   (2006.01)

(52) U.S. Cl. .................... 523/109; 528/13; 524/588
(58) Field of Classification Search ............... 528/13; 523/109; 524/588
See application file for complete search history.

(56) References Cited

U.S. PATENT DOCUMENTS

| 6,743,883 B1 * | 6/2004 | Frances et al. ............... 528/13 |
| 6,747,071 B1 * | 6/2004 | Frances ....................... 522/148 |
| 6,867,242 B1 * | 3/2005 | Frances et al. ............... 522/31 |

* cited by examiner

Primary Examiner—Margaret G. Moore

(57) ABSTRACT

The present invention relates to silicone-based dental compositions based on a functionalized silicone crosslinkable and/or polymerizable by heat-process. These novel dental compositions are polymerizable and/or crosslinkable in an oral environment, have markedly improved qualities, in particular as regards the very marked reduction in the phenomenon of shrinkage of the materials and prostheses obtained from said compositions. These novel dental compositions are particularly advantageous in terms of reactivity; they are crosslinkable and/or polymerizable by heat, which makes it possible to use conventional crosslinking/polymerization methods and furthermore at temperatures of less than 150° C. This reactivity is in particular due to the presence of a particular type of initiator based on a boron derivative; That initiator is active in low concentration and advantageously requires only small quantities of energy to carry out the crosslinkage/polymerization.

16 Claims, No Drawings

DENTAL COMPOSITION BASED ON A FUNCTIONALIZED SILICONE CROSSLINKABLE AND/OR POLYMERIZABLE BY HEAT-PROCESS

This application is an application under 35 U.S.C. Section 371 of International Application Number PCT/FR01/04044 filed on Dec. 18, 2001.

The field of the invention is that of dental compositions. More precisely, the dental compositions used in the context of the present invention are based on crosslinkable and/or polymerizable functionalized silicone, and can be used for producing dental prostheses, artificial teeth and dental restoration materials.

Up until now, to produce dental compositions for the preparation of dental prostheses or of dental restoration materials, it is possible to use resins based on photopolymerizable acrylates. These ready-to-formulate products exhibit however upon use problems of irritation and potential problems of toxicity.

In addition, these products have the major disadvantage of causing high volume shrinkage during their polymerization, which makes their use complex and difficult for the production of dental prostheses or of dental restoration materials. Problems of attachment due to the volume shrinkage or to the lack of adherence of the polymers used are in particular observed.

The object of the present invention is to provide novel silicone-based dental compositions which do not exhibit the disadvantages of the prior art. These novel dental compositions, which are polymerizable and/or crosslinkable in an oral environment, have markedly improved qualities, in particular as regards the very marked reduction in the phenomenon of shrinkage of the materials and prostheses obtained from said compositions.

These novel dental compositions are particularly advantageous in terms of reactivity; they are crosslinkable and/or polymerizable by heat, which makes it possible to use conventional crosslinking/polymerization methods and furthermore at temperatures of less than 150° C. This reactivity is in particular due to the presence of a novel type of initiator based on a boron derivative; indeed, the latter is active in low concentration and advantageously requires only small quantities of energy to carry out the crosslinkage/polymerization.

Accordingly, the claimed dental compositions are therefore found to be particularly advantageous in terms of efficacy during use and in terms of profitability and cost for industrial processes.

The heat-polymerizable and/or crosslinkable dental composition according to the invention comprises:
(1) 1 to 99% by weight, and preferably from 5 to 50%, of at least one crosslinkable and/or polymerizable silicone oligomer or polymer which is liquid at room temperature or which is heat-meltable at a temperature of less than 100° C., and which comprises:
at least one unit of formula (FS):

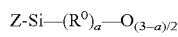

in which:
a=0, 1 or 2,
$R^0$, identical or different, represents an alkyl, cycloalkyl, aryl, vinyl, hydrogeno or alkoxy radical, preferably a $C_1$–$C_6$ lower alkyl,
Z, identical or different, is an organic substituent comprising at least one epoxy and/or alkenyl ether and/or oxetane and/or dioxolane and/or carbonate reactive functional group, and preferably Z being an organic substituent comprising at least one epoxy and/or dioxolane reactive functional group,
and at least two silicon atoms;
(2) from 5 to 90% by weight, and preferably 10 to 80%, of at least one dental filler;
(3) from 0.001 to 5% by weight of at least one heat-activatable polymerization and/or crosslinking initiator comprising a boron derivative of formula (I) and/or its solvated form(s):

in which:
the symbols R' are identical or different and represent:
a linear or branched $C_{1-12}$, preferably $C_1$–$C_8$, alkoxy radical, optionally substituted with at least one electron-attracting element, in particular a halogen atom (fluorine most particularly), or an electron-attracting group such as for example the $CF_3$, $NO_2$ and $CN$ groups,
a phenyl radical substituted with at least (i) an electron-attracting element, in particular a halogen atom (fluorine most particularly), (ii) an electron-attracting group, in particular a $CF_3$, $NO_2$ or $CN$ group, or (iii) a saturated, unsaturated or aromatic, mono- or polycyclic, linear or branched $C_1$–$C_{12}$, preferably $C_1$–$C_8$, hydrocarbon radical, preferably substituted with at least one element which is a halogen atom or a mono-, poly- or perhalogenated, linear or branched $C_1$–$C_{12}$ alkyl radical, and
an aryl radical containing at least two aromatic rings such as biphenyl, naphthyl, optionally substituted with at least one electron-attracting element, in particular a halogen atom (fluorine most particularly), or an electron-attracting group, in particular a $CF_3$, $NO_2$ or $CN$ group,
two groups R' may be linked to each other so as to constitute, with the boron atom to which they are attached, a 5- or 10-atom ring, it being possible for said ring to be saturated, unsaturated bridged and/or aromatic and to comprise one or more heteroatoms chosen from hydrogen, nitrogen and boron atoms, it being possible for the boron atom present in said ring to be substituted itself with a radical as defined for A or R' in general formula I;
the symbols A represent independently of each other:
a halogen atom, or
a hydroxyl radical;
x represents 0 or the integer 1 or 2 and y the integer 1, 2 or 3 with the sum of x+y being equal to 3.

In general, the heat activation is carried out at temperatures of less than 150° C., preferably of less than 100° C. or even in particular at room temperature for placing in the mouth.

The boron-derived initiators used in the dental compositions in accordance with the invention are generally very hygroscopic compounds. Consequently, these compounds may exist in the form of a mixture of the compound as defined in general formula (I) and its different hydrated form(s). Likewise, during the formulation of this initiator with a solvent, the formation of solvated derivatives is observed. This phenomenon may be observed with aprotic solvents such as ethers, esters and silicones or protic solvents such as alcohols, carboxylic acids, silanols, amines, thiols, water or mixtures thereof.

Consequently, the present invention also extends to these solvated forms.

These initiators may additionally be combined with a conventional initiator such as a cationic photoinitiator. This is particularly advantageous in terms of profitability, since it is thus possible to significantly reduce the effective quantity of conventional initiator of this type. The crosslinkage and/or polymerization is moreover fully achieved.

More preferably, the symbols R' in the general formula (I) are chosen so as to confer on the boron atom to which they are attached a steric hindrance sufficient to ensure effective protection in particular for preventing its oxidation and/or hydration. In the case in point, the initiators of general formula (I) in which at least one of the symbols R' and preferably at least two of them represent a phenyl or aryl radical are particularly advantageous.

Likewise, it is advantageous for the symbols R' to be substituted and in particular with electron-attracting elements and/or groups so as to give said boron atom an electronegativity which is compatible with its electrophilic properties. Accordingly, initiators of general formula (I) in which the symbols R' contribute overall with the symbols A to a $\sigma_p$ at least equal to that of 3 radicals ($C_6H_4F$) are found to be particularly effective.

Particularly preferred according to the invention are the initiators corresponding to general formula (Ia):

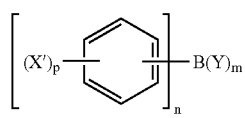

in which:
n represents an integer between 1 and 3 and m an integer between 0 and 2 with the sum of n and m being equal to 3,
the symbols Y are identical or different and represent
a) a hydroxyl group,
b) a halogen atom,
c) a linear or branched $C_1$–$C_{12}$, preferably $C_1$–$C_8$, alkoxy radical, preferably substituted with at least one electron-attracting element such as a halogen atom and in particular a fluorine atom,
d) two groups Y may be linked to each other so as to constitute with the boron atom to which they are attached a $C_5$–$C_{10}$ ring with said ring being possibly saturated, unsaturated, bridged and/or aromatic and possibly comprising one or more heteroatoms chosen from oxygen, nitrogen and boron atoms, it being possible for the boron atom present in said ring to be substituted itself with a radical as defined for Y in general formula (Ia) and
the symbols X' are identical or different and represent
a halogen atom, preferably a fluorine atom,
a saturated, unsaturated or aromatic, mono- or polycyclic, linear or branched $C_1$–$C_{12}$, preferably $C_1$–$C_8$, hydrocarbon radical, preferably substituted with at least one electron-attracting element such as a halogen atom and in particular a fluorine atom or a mono-, poly- or perhalogenated, linear or branched $C_1$–$C_{12}$, preferably $C_1$–$C_8$, alkyl radical with in particular fluorine as halogen atom, and
the indices p are identical or different and represent an integer between 0 and 5, with preferably at least one of the symbols p being greater than 3 and more preferably equal to 5.

The initiators of general formula (Ia) in which Y corresponds to the definitions a), b) and c) are particularly advantageous.

By way of representation of the claimed initiators, the following compounds may be more particularly mentioned:

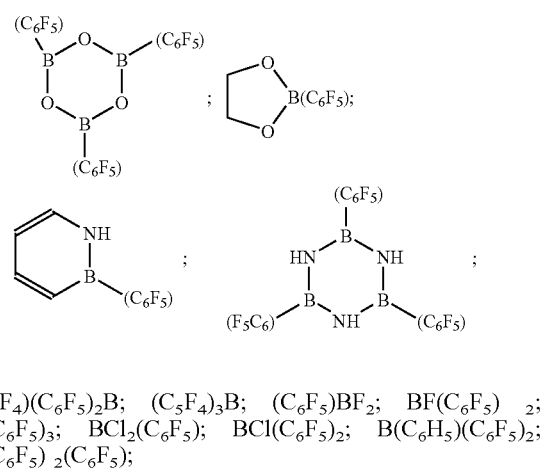

$(C_5F_4)(C_6F_5)_2B$; $(C_5F_4)_3B$; $(C_6F_5)BF_2$; $BF(C_6F_5)_2$; $B(C_6F_5)_3$; $BCl_2(C_6F_5)$; $BCl(C_6F_5)_2$; $B(C_6H_5)(C_6F_5)_2$; $B(C_6F_5)_2(C_6F_5)$;

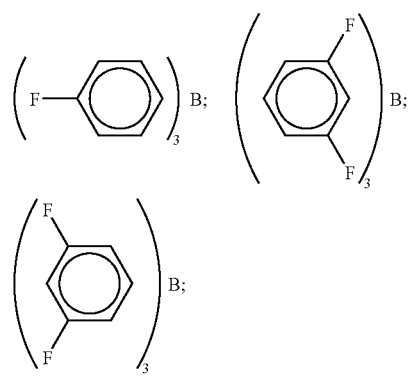

$[C_6H_4(mCF_3)]_3B$;

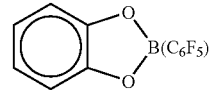

$[C_6H_4(pOCF_3)]_3B$; $(C_6F_5)B(OH)_2$; $[C_6H_3bis(mCF_3)_2]_3B$; $(C_7H_{11})B(C_6F_5)_2$;

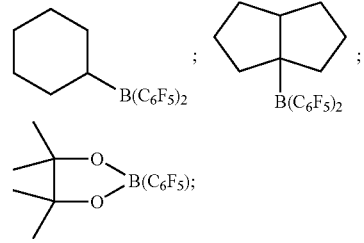

$(C_6F_5)_2B(OC_2H_5)$; $(C_6F_5)_2BOH$;

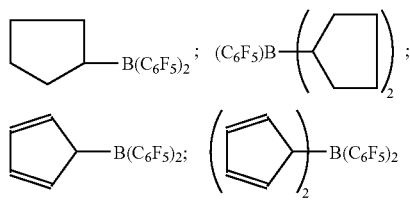

The initiators used in the compositions according to the invention may be used as obtained at the end of their method of preparation, for example in solid or liquid form, or as a solution in at least one appropriate solvent. The term solvent covers in the present case the products solubilizing the solid initiators and the products diluting the liquid or solid initiators.

Preferably, the initiators are generally used in solution in a solvent. The proportions by weight between the initiator(s), on the one hand, and the solvent, on the other hand, are between 0.1 and 99 parts per 100 parts of solvent, and preferably from 10 to 50 parts.

This initiator solution is therefore used to prepare a bath with the silicone oligomer(s) (and/or polymer(s) containing crosslinkable functional groups, such that the concentration of initiator or initiators present is between 0.01 and 5% by weight in said bath, and preferably between 0.05 and 0.5%.

The solvents which can be used for the initiators are very many and varied and are chosen from the initiator used and the other constituents of the composition of the invention. In general, the solvents may be alcohols, esters, ethers, ketones, water in trace amounts and carbonates.

The alcohols commonly used are para-tolylethanol, isopropylbenzyl alcohol, benzyl alcohol, methanol, ethanol, propanol, isopropanol and butanol. The ethers commonly used are 2-methoxyethanol, 2-ethoxyethanol and diethylene glycol. The customary esters are dibutyl maleate, dimethylethyl malonate, methyl salicylate, dioctyl adipate, butyl tartrate, ethyl lactate, n-butyl lactate, and isopropyl lactate. Other solvents which can be used for the bath of the initiator and entering into the other categories of solvents cited above are acetonitrile, benzonitrile, acetone, cyclohexanone and tetrahydrofuran.

In addition, among the solvents which can be used to dissolve the initiator(s), some types of proton-donating organic solvents and some types of hydroxylated carboxylic acid esters also have the properties of significantly improving their performance in terms of reactivity and kinetics.

As indicated above, in solution, the initiator in the compositions according to the invention can change to a solvated form.

The various forms can coexist in the solvent under the effect of an equilibrium. By way of representation of these solvation phenomena, there may be mentioned in particular:

Water $H_2O + B(Ar)_3 \rightleftharpoons H^+[B(Ar)_3(OH)]^-$

Alcohol $R^*OH + B(Ar)_3 \rightleftharpoons H^+[B(Ar)_3(OR^*)]^-$

Amine $R^*_2NH + B(Ar)_3 \rightleftharpoons H^+[B(Ar)_3(NR^*_2)]^-$

Amine $R^*_3N + B(Ar)_3 \rightleftharpoons B(Ar)_3(NR^*_3)$

Acid $R^*COOH + B(Ar)_3 \rightleftharpoons H^+[B(Ar)_3(OCOR^*)]^-$

The type of initiator used in the compositions according to the invention also extends to the solvated forms of the claimed initiators.

In the context of the invention, the reactive functional groups Z of the silicone polymer or oligomer (1) may be highly varied.

However, according to an advantageous feature of the invention, particularly advantageous dental compositions are obtained when the silicone oligomer or polymer (1) comprises at least one unit (FS) in which Z represents an organic substituent Z1 comprising at least one epoxy and/or dioxolane reactive functional group, and preferably at least one epoxy reactive functional group.

According to two advantageous alternatives of the present invention, the silicone oligomer or polymer (1) with at least one epoxy and/or dioxolane reactive functional group Z1, and preferably at least one epoxy reactive functional group may:

(i) either comprise only this (these) type(s) of reactive functional group(s) Z1, (ii) or comprise other reactive functional groups Z such as the alkenyl ether, oxetane and/or carbonate reactive functional groups Z2.

In the case of the first alternative (i), the dental composition may also comprise other silicone oligomers and/or polymers comprising other reactive functional groups Z2 such as alkenyl ether, oxetane and/or carbonate functional groups and optionally reactive functional groups Z1.

By way of examples of reactive functional groups Z, they may be chosen in particular from the following radicals:

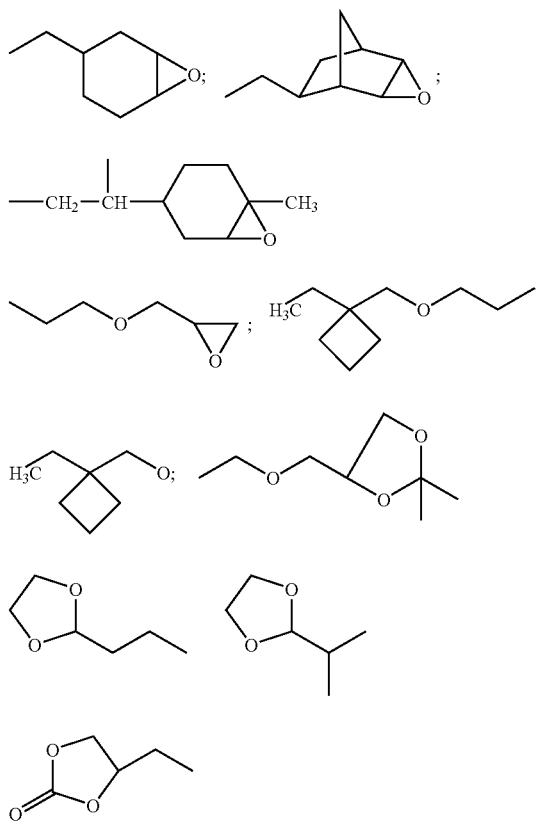

—(CH$_2$)$_3$—O—CH═CH$_2$; —(CH$_2$)$_3$—O—CH═CH—R"
with R" representing a linear or branched C$_1$–C$_6$ alkyl radical.

By way of examples, the silicone polymer or oligomer consists of at least one silicone having the following average formula:
a) 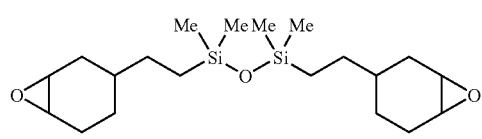
b) 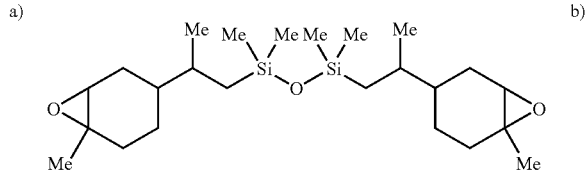
c) 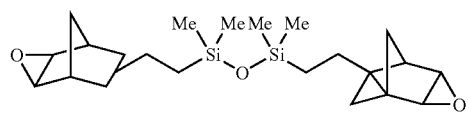
d) 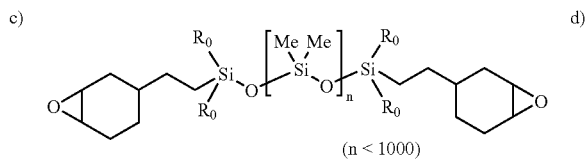
(n < 1000)
e) 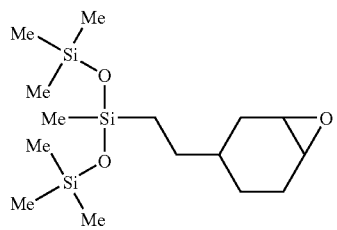
f) 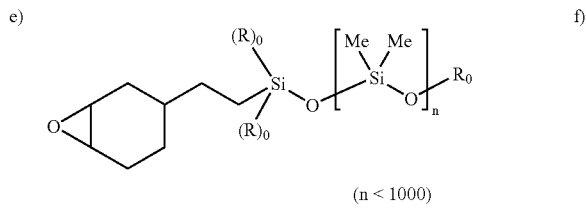
(n < 1000)
g) 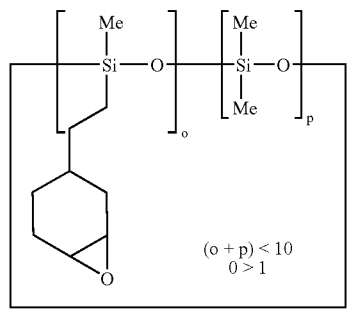
(o + p) < 10
o > 1
h) 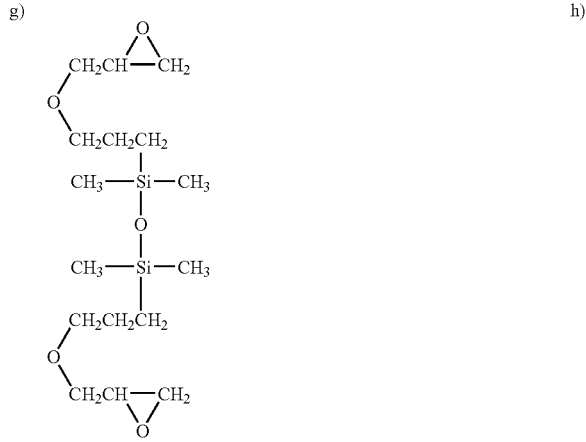
i) 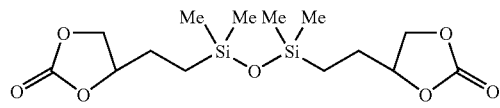
j) 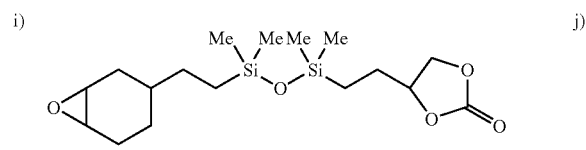
k) 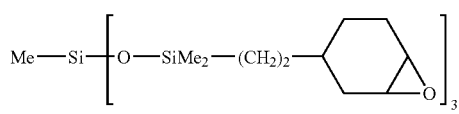
l) 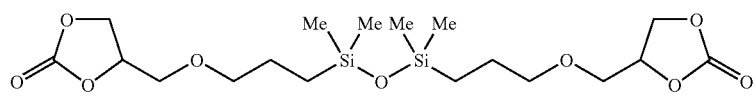
m) 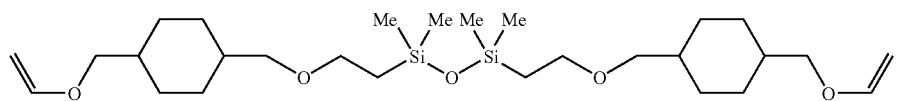

-continued

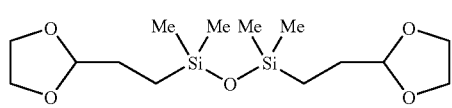 n)

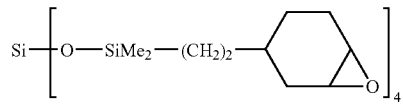 o)

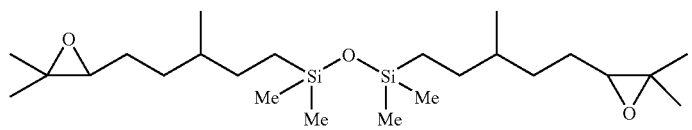 p)

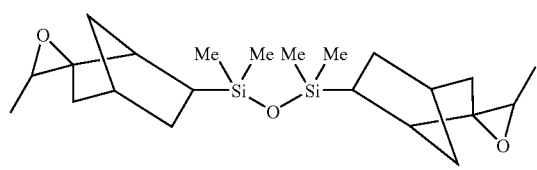 q)

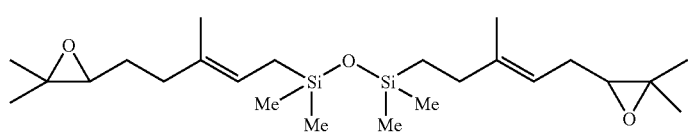 r)

According to an advantageous feature of the invention, in addition to the oligomers and/or polymers of a silicone nature, the dental composition may comprise crosslinkable and/or polymerizable monomers, oligomers and/or polymers of an organic nature. These may be chosen in particular from the following organic species:

α1.1) cycloaliphatic epoxides and in particular:
epoxides of the 3,4-epoxicyclohexyl-methyl-3',4'-epoxycyclohexanecarboxylate type:

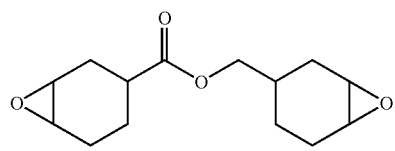

bis(3,4-epoxycyclohexyl)adipate,
epoxides of the glycidic type such as: neopentyl glycol, diglycidyl ether, 1,4-dibutanediol diglycidyl ether, dodecyl glycidyl ether, cyclohexanedimethanol diglycidyl ether, trimethylolpropane triglycidyl ether, and the epoxides described in the documents U.S. Pat. No. 6,084,111 and U.S. Pat. No. 6,075,155;

α1.2) noncycloaliphatic epoxides, and in particular:
epoxides such as those resulting from the condensation of Bisphenol A and epichlorohydrin and of the type:
di- and triglycidyl ethers of alkoxylated Bisphenol A of 1,6-hexanediol, of glycerol, of neopentyl glycol and of propanetrimethylol,
or glycidyl ethers of Bisphenol A,
alpha-olefin epoxides, NOVOLAC epoxides, epoxidized soybean oil, epoxidized linseed oil, and epoxidized polybutadiene;

α2) terpene oxides, and in particular: limonene dioxide; myrcene 6,7-epoxide or myrcene dioxide, dihydromyrcene 6,7-epoxide; pinene oxide; 5-ethylidenenorbornene 5,8-epoxide; and 5-vinyl-2,3-epoxynorbornene;

α3) linear or cyclic alkenyl ethers, and in particular:
vinyl ethers, in particular octyl vinyl ether, dodecyl vinyl ether (DDVE), cyclohexyl vinyl ether (CVE), butanediol divinyl ether (BDVE), butanediol monovinyl ether (HBVE), cyclohexane dimethanol divinyl ether (CHDVE), cyclohexane dimethanol monovinyl ether (CHMVE), triethylene glycol divinyl ether (DVE-3) and the vinyl ethers of formula:

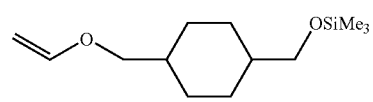

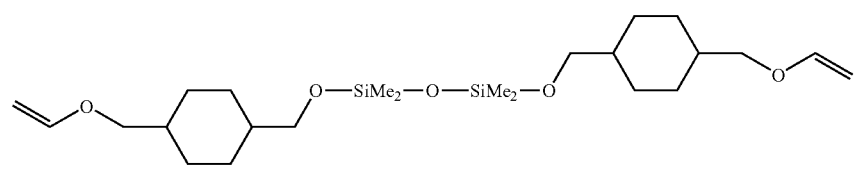

propenyl ethers, and butenyl ethers;

α4) polyols, and preferably the compound of formula:

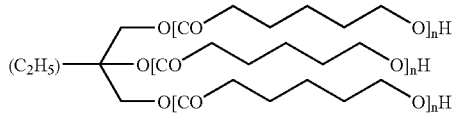

α5) oxetanes, and for example the oxetanes having the following formulae:

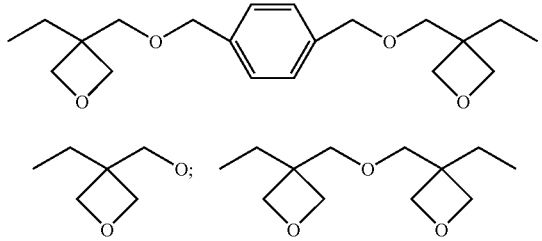

Various types of fillers can be used for preparing the compositions according to the invention. The fillers are chosen according to the final use of the dental composition: these affect important properties such as appearance, as well as the mechanical and physical properties of the material obtained after crosslinking and/or polymerization of the dental composition.

As reinforcing filler, there may be used treated or untreated pyrogenic silica fillers, amorphous silica fillers, quartz, glass or nonglassy fillers based on oxides of zirconium, boron, barium, calcium, fluorine, aluminum, titanium, strontium, zinc, borosilicates, aluminosilicates, talc, spherosil, ytterbium trifluoride, fillers based on polymers in ground powder form, such as inert or functionalized methyl polymethacrylates, polyepoxides or polycarbonates.

By way of example, there may be mentioned:

inert fillers based on methyl polymethacrylate LUXAS-ELF from the company UGL, which can be used in the dental field and which are pigmented in pink, hexamethyldisilazane-treated fumed silica fillers having a specific surface area of 200 m²/g, untreated fumed silica fillers (Aerosil product A-200 marketed by DEGUSSA).

According to an advantageous variant of the invention, the fillers and in particular the silica fillers are treated before use at 120° C. with a quantity of less than 10% w/w of silicone comprising at least one unit of formula:

$$Z'-Si-(R^0)_a-O_{(3-a)/2}$$

such that Z' has the same definition as Z a=0, 1, 2 or 3 with at least one silicon atom.

There may be mentioned by way of example the polymer described below with Z=epoxide and Z=trialkoxysilyl

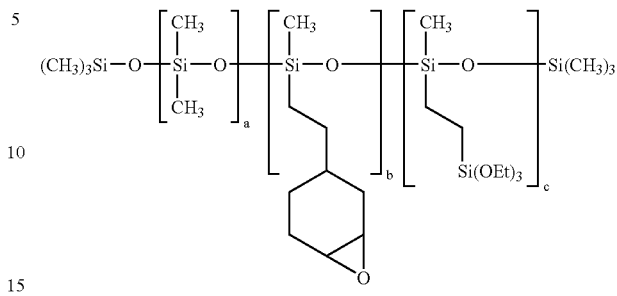

a = 9; b = 2; c = 2

In this case for the treatment of silicone-containing filler(s), in particular silica, with this type of polymer, the material obtained after crosslinking has a mechanical strength, a modulus of elasticity and a resistance to compression which are markedly improved.

In addition to the reinforcing fillers, pigments may be used to color the dental composition according to the invention envisaged and the ethnic groups.

For example, red pigments are used in the presence of microfibers for the dental compositions used for the preparation of dental prostheses in order to simulate the blood vessels.

Pigments based on metal oxides (iron and/or titanium and/or aluminum and/or zirconium oxides, and the like) are also used for the dental compositions used for the preparation of restoration material, in order to obtain a crosslinked material having an ivory or white color.

Other additives may be incorporated into the dental compositions according to the invention. For example, biocides, stabilizers, flavoring agents, plasticizers and adherence promoters.

Among the additives which may be envisaged, there will be advantageously used crosslinkable and/or polymerizable coreagents of the organic type. These coreagents are liquid at room temperature or are hot-meltable at a temperature of less than 100° C., and each coreagent comprises at least two reactive functional groups such as oxetane-alkoxy, oxetane-hydroxyl, oxetane-alkoxysilyl, carboxyl-oxetane, oxetane-oxetane, alkenyl ether-hydroxyl, alkenyl ether-alkoxysilyl, epoxy-alkoxy, epoxy-alkoxysilyls, dioxolane-dioxolane-alcohol, and the like.

The dental compositions according to the invention can be used in the field or dental prosthesis, the field of dental restoration material, and in the field of artificial teeth. They can be formulated in monocomponent form or in bicomponent form.

In the context of the invention:

the dental compositions for dental prosthesis comprise from 25 to 90% by weight of silicone and from 10 to 75% of filler(s) and an effective quantity of the initiator of formula (I), the dental compositions for artificial teeth comprise from 5 to 50% by weight of silicone and from 50 to 95% of filler(s) and an effective quantity of the initiator of formula (I), the dental compositions for dental restoration comprise from 15 to 50% by weight of silicone and from 50 to 95% of filler(s) and an effective quantity of the initiator of formula (I).

The preparations for dental prostheses, artificial teeth and dental restoration material are carried out according to the customary techniques in the field.

The stability before crosslinking and/or polymerization of the monocomponent or bicomponent dental compositions may be provided by derivatives with amine functional groups, in particular sterically hindered amines such as amines of the HALS type. It is possible to use in particular the amines mentioned in the document WO 98/07798.

It should be noted that the products obtained from the dental composition according to the invention are nonporous. Thus, after an optional polishing with the aid of a felt brush, for example, the surface of the dental prostheses obtained is smooth and bright and therefore does not require the use of varnish.

The application in the field of dental prosthesis is essentially that of the joined prosthesis, which can be divided into two types:

full prosthesis (upper and lower maxillae) in the case of a patient with absolutely no teeth partial prosthesis due to the absence of several teeth, resulting either in a provisional prosthesis, or a skeleton brace.

This application also relates to the production of borders and the repair of prosthesis (rebasing by casting or injection).

In the case of application of the dental composition to a tooth, either the tooth may be pretreated with a bonding primer or the dental composition may be prepared as a mixture with a bonding primer before its use. However, it is not essential to use a bonding primer in order to use the dental composition according to the invention.

The dental composition being nontoxic and polymerizable in thick layers, it is not essential to polymerize the material in successive layers. In general, a single injection of the dental composition is sufficient.

EXAMPLES AND TESTS

The following examples and tests are given by way of illustration. They make it possible in particular to better understand the invention and to demonstrate some of its advantages and to illustrate a few of its variant embodiments. Examples 1 to 8 and 10 relate to predental compositions [(with no filler(s)] which can be used in particular for dental prosthesis. Examples 9 and 11 relate to dental compositions [with filler(s)].

The products used in the compositions of the examples are the following:

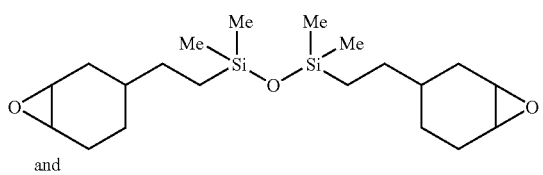

and

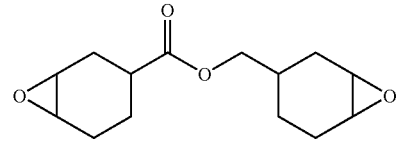

(II)

The life span of the "ready-to-crosslink" compositions is determined by the addition of a sterically hindered organic amine marketed under the name Tinuvin 765 by the company Ciba. The life span corresponds to the time during which the composition can be handled.

Examples 1 to 6

In each example, the oligomer of formula (I) is introduced into a mold for dental prostheses in an amount of 100 g over a thickness of 10 mm. 2.8 g of an isopropanol solution of borane $B(C_6F_5)_3$ at 3% by weight are then added at room temperature; this solution additionally contains a sterically hindered amine (product Tinuvin 765®).

In each example, the amine concentration of the borane solution is different. The molar ratios R of the amine expressed as a function of nitrogen relative to that of the borane expressed as a function of boron are given in table 1 below.

For each crosslinked composition, the gel time is measured at 20° C. and the Shore D hardness is measured (according to the DIN 43505 standard), which is obtained after triggering the polymerization reaction while allowing a return to a room temperature of 22° C.±2 after 24 h and after demolding. The materials obtained have no porosities.

TABLE 1

| Example | % borane | % Tinuvin | R | Gel time (min) | Shore D hardness (24 h) |
|---|---|---|---|---|---|
| 1 | 3 | 0.66 | 0.49 | 0.5 | 85 |
| 2 | 3 | 1.26 | 0.93 | 1 | 85 |
| 3 | 3 | 1.325 | 1 | 3 | 85 |
| 4 | 3 | 1.4 | 1.04 | 3.5 | 85 |
| 5 | 3 | 1.5 | 1.11 | 10 | 85 |
| 6 | 3 | 1.66 | 1.23 | 600 | 85 |

Example 7

This example relates to a composition based on 100 g of oligomer (I) mixed with 2.8 g of borane initiator solution containing 1.66% by weight of Tinuvin 765 and 3% by weight of borane. The composition is crosslinked in an oven at 60° C. for 10 minutes.

The Shore D hardness measured after cooling is 85. The material obtained is completely transparent and colorless. The volume shrinkage of the material with no fillers, measured by pycnometry, is between 3 and 4%.

Example 8

A borane solution is obtained by mixing 0.48 g of borane $B(C_6F_5)_3$ hydrate at 18% in isopropanol, 2.3 grams of 3-ethyl-(3-hydroxymethyl)oxetane and 39 mg of the product Tinuvin 765®.

2.8 g of this solution are added to 100 g of oligomer of formula (I). The mixture is stable at 20° C. for more than 4 hours; the crosslinking is carried out at 60° C. in order to give a material having a Shore D hardness equal to 50 after 24 h.

Example 9

A plastic pot containing 12.5 g of oligomer (I); 0.5 g of solution of initiator of example 8; 25 g of quartz; and 12.5 g of fumed silica having a specific surface of 200 m²/g, is introduced into a Hauschild Speedmixer DAC150® type mixer.

The mixer is successively started three times 5 seconds after introducing the quartz and three times 5 seconds during the introduction of the fumed silica such that the temperature of the mixture does not exceed 40° C.

The mixture is then crosslinked at 80° C. for 10 minutes and a material having a Shore D hardness greater than 90 is obtained. The volume shrinkage is less than 1% (measured by pycnometry).

Example 10

A borane solution is obtained by mixing 0.48 g of borane $B(C_6F_5)_3$ hydrate at 18% in isopropanol, 2.3 g of resin (II) and 39 mg of the product Tinuvin 765®.

2.8 g of this solution are added to 100 g of oligomer (I). The mixture is stable at 20° C. for more than 4 hours; the crosslinking is carried out at 60° C. in order to give a material having a Shore A hardness greater than 90 and a Shore D hardness equal to 50 after 24 h.

Example 11

A bicomponent mixture consisting of a composition A and a composition B is prepared.

The composition A is prepared in a Hauschild Speedmixer DAC50® mixer from 12.5 g of oligomer (I) and 12.5 g of powdered polymethyl methacrylate filler (product LUXAS-ELF®). The composition B consists of a solution of initiator according to example 10.

The composition A is then mixed using a small static mixer with 2 g of the composition B. The mixture obtained is crosslinked at room temperature in 1 hour (or in 10 minutes at 60° C.).

The invention claimed is:
1. A dental composition comprising:
   (1) 1 to 99% by weight, of at least one crosslinkable or polymerizable silicone oligomer or polymer which is liquid at room temperature or which is heat-meltable at a temperature of less than 100° C., comprising: at least one unit of formula (FS):

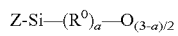

wherein:
   a=0, 1 or 2,
   R⁰, identical or different, represents an alkyl, cycloalkyl, aryl, vinyl, hydrogeno or alkoxy radical,
   Z, identical or different, is an organic substituent comprising at least one epoxy, alkenyl ether, oxetane, dioxolane, or carbonate reactive functional group, and at least two silicon atoms;
   (2) from 5 to 90% by weight, of at least one dental filler;
   (3) from 0.001 to 5% by weight of at least one heat-activatable polymerization or crosslinking initiator comprising a boron derivative of formula (I) or its solvated form(s):

 (I)

wherein:
   the symbols R' are identical or different and represent:
   a linear or branched $C_{1-12}$, preferably $C_1$–$C_8$, alkoxy radical, optionally substituted with at least one electron-attracting element, or an electron-attracting group,
   a phenyl radical substituted with at least (i) an electron-attracting element, (ii) an electron-attracting group, or (iii) a saturated, unsaturated or aromatic, mono- or polycyclic, linear or branched $C_1$–$C_{12}$, optionally substituted with at least one element which is a halogen atom or a mono-, poly- or perhalogenated, linear or branched $C_1$–$C_{12}$ alkyl radical, and
   an aryl radical containing at least two aromatic rings, optionally substituted with at least one electron-attracting element, or an electron-attracting group,
   two groups R' are optionally linked to each other so as to constitute, with the boron atom to which they are attached, a 5- or 10-atom ring, it being possible for said ring to be saturated, unsaturated bridged or aromatic and to comprise one or more heteroatoms chosen from hydrogen, nitrogen and boron atoms, it being possible for the boron atom present in said ring to be substituted itself with a radical as defined for A or R' in general formula (I);
   the symbols A represent independently of each other:
   a halogen atom, or
   a hydroxyl radical;
   x represents 0 or the integer 1 or 2 and y the integer 1, 2 or 3 with the sum of x+y being equal to 3.

2. The dental composition as claimed in claim 1, comprising:
   (1) from 5 to 50%, of the crosslinkable or polymerizable silicone oligomer or polymer, having units of formula (FS) wherein:
   R⁰ is a $C_1$–$C_6$ lower alkyl,
   Z is epoxy or a dioxolane reactive functional group;
   (2) from 10 to 80%, of at least one dental filler;
   (3) wherein, in the formula (I) of the boron derivative or its solvated form(s):
   the symbols R' are $C_1$–$C_8$, alkoxy radical, optionally substituted with at least one halogen atom, or an electron-attracting group being $CF_3$, $NO_2$ or CN,
   a phenyl radical substituted with at least (i) a halogen atom, (ii) an electron-attracting group, being a $CF_3$, $NO_2$ or CN group, or (iii) a saturated, unsaturated or aromatic, mono- or polycyclic, linear or branched $C_1$–$C_8$, hydrocarbon radical, substituted with at least one element which is a halogen atom or a mono-, poly- or perhalogenated, linear or branched $C_1$–$C_{12}$ alkyl radical, and
   an aryl radical being biphenyl or naphthyl, optionally substituted with at least one halogen atom, or an electron-attracting groupbeing a $CF_3$, $NO_2$ or CN group.

3. The composition as claimed in claim 1, wherein the symbols R' are chosen so as to confer on the boron atom to which they are attached a steric hindrance sufficient to ensure effective protection against oxidation or hydration phenomena.

4. The dental composition as claimed in claim 1, wherein the symbols R' contribute overall with the symbols A to a ohd p at least equal to that of 3 radicals ($C_6H_4F$).

5. The dental composition as claimed in claim 1, wherein the initiator (3) corresponds to general formula (Ia):

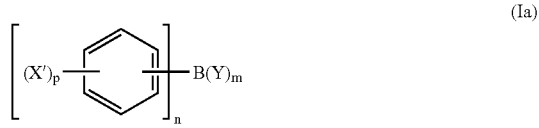
(Ia)

wherein:
n represents an integer between 1 and 3 and m an integer between 0 and 2 with the sum of n and m being equal to 3,
the symbols Y are identical or different and represent
a) a hydroxyl group,
b) a halogen atom,
c) a linear or branched $C_1$–$C_{12}$, optionally substituted with at least one electron-attracting element,
d) two groups Y may be linked to each other so as to constitute with the boron atom to which they are attached a $C_5$–$C_{10}$ ring with said ring being possibly saturated, unsaturated, bridged or aromatic and possibly comprising one or more heteroatoms being oxygen, nitrogen or boron atoms, it being possible for the boron atom present in said ring to be substituted itself with a radical as defined for Y in general formula (Ia) and
the symbols X' are identical or different and represent a halogen atom,
a saturated, unsaturated or aromatic, mono- or polycyclic, linear or branched $C_{1-12}$, preferably $C_1$–$C_8$, hydrocarbon radical, optionally substituted with at least one element which is a halogen atom or a mono-, poly- or perhalogenated, linear or branched $C_1$–$C_{12}$ alkyl radical, and
the indices p are identical or different and represent an integer between 0 and 5.

6. The dental composition as claimed in claim 5, wherein the symbols Y are $C_1$–$C_8$, alkoxy radical, optionally substituted with at least one halogen atom, and
the symbols X' are $C_1$–$C_8$, hydrocarbon radical, optionally substituted with at least one halogen atom or a mono-, poly- or perhalogenated, linear or branched $C_1$–$C_{12}$ alkyl radical, and
the symbols p are equal to 5.

7. The dental composition as claimed in claim 1, wherein Z is an epoxy reactive functional group.

8. The dental composition as claimed in claim 1, wherein the oligomer or polymer (1) further comprises other reactive functional groups Z.

9. The dental composition as claimed in claim 8, wherein the other reactive functional groups Z are alkenyl ether, oxetane or carbonate reactive functional groups Z2.

10. The dental composition as claimed in claim 7, wherein the reactive functional group is one of the following formulas.

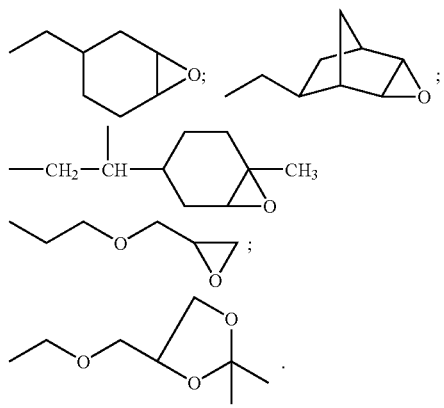

11. The dental composition as claimed in claim 1, further comprising crosslinkable or polymerizable monomers, oligomers or organic polymers.

12. The dental composition as claimed in claim 1, further comprising at least one stabilizing compound with amine functional groups.

13. The dental composition as claimed in claim 2, wherein said amine is a sterically hindered amine.

14. A dental prosthese made with a dental composition as defined in claim 1.

15. A dental restoration material made with a dental composition as defined in claim 1.

16. An artificial tooth made with a dental composition as defined in claim 1.

* * * * *